United States Patent [19]

Sherman

[11] 4,367,157

[45] * Jan. 4, 1983

[54] SOFT CONTACT LENS AMBIENT TEMPERATURE DISINFECTANT SOLUTION CONTAINING ASCORBIC ACID OR SALT THEREOF

[75] Inventor: Guy J. Sherman, Mandeville, La.

[73] Assignee: Sherman Laboratories, Inc., Abita Springs, La.

[ * ] Notice: The portion of the term of this patent subsequent to Oct. 26, 1999, has been disclaimed.

[21] Appl. No.: 228,562

[22] Filed: Jan. 26, 1981

Related U.S. Application Data

[63] Continuation-in-part of Ser. No. 37,645, May 10, 1979.

[51] Int. Cl.$^3$ ............................ C11D 3/48; C11D 1/04
[52] U.S. Cl. .................................... 252/106; 252/173; 252/546; 252/DIG. 14
[58] Field of Search .............. 252/106, 174.23, 174.24, 252/173, DIG. 14; 428/78, 80, 146; 134/40, 42

[56] References Cited

U.S. PATENT DOCUMENTS 3,329,607  7/1967  Colobert .......................... 252/181 X
4,126,587  11/1978  Sibley et al. ...................... 134/40 X
4,199,469  4/1980  Walzer .............................. 134/41 X

FOREIGN PATENT DOCUMENTS 52-18708  2/1977  Japan .

*Primary Examiner*—P. E. Willis, Jr.
*Attorney, Agent, or Firm*—Winburn & Gray, Ltd.

[57] ABSTRACT

Aqueous compositions for the ambient temperature or cold disinfection of soft contact lenses during non-wearing periods is provided. The composition includes water and a disinfectant composition comprising an effective amount of an ascorbic acid compound for killing bacteria, generally between about 0.1% and 20% by weight of the total aqueous composition, calculated as ascorbic acid. The disinfectant composition may also include a potentiating agent to further enhance the kill factor of ascorbic acid with respect to fungi, yeasts and viruses.

10 Claims, No Drawings

SOFT CONTACT LENS AMBIENT TEMPERATURE DISINFECTANT SOLUTION CONTAINING ASCORBIC ACID OR SALT THEREOF

RELATED APPLICATIONS

This application is a continuation-in-part application of application Ser. No. 37,645 filed May 10, 1979.

BACKGROUND OF THE INVENTION

Just as there are marked differences in the structure and composition of hard and soft contact lenses, there are also marked differences in the maintenance and care or treatment of the various types of hard, semi-hard and soft lenses. While patient care and treatment of hard contact or conventional contact lenses is relatively simple and uncomplicated, the proper care and treatment of the newer soft and hydrophilic lenses has proved to be more complex and time consuming.

The primary difference between the conventional hard contact lens and the more complex soft lenses is the marked increase in the polar or water attracting centers of the hydrophilic gel material. It is this property of the hydrophilic gel lens that gives the soft lens its own unique physical properties and clinical behaviour. This polar or water attracting center of the gel material is represented in the hydroxyethyl methacrylate bond as a hydroxyl group (—OH) which attracts and holds large amounts of water. It is this high water content held in the expanded matrix of the hydrophilic gel lens which leads to the special difficulties in and disinfecting or asepticising the soft hydrophilic lens. The hydrophilic nature of soft contact lenses makes the lenses vulnerable to bacterial contamination. While studies have domonstrated that bacteria cannot penetrate the actual intramolecular pores of the hydrophilic lens, except in defective lenses, the bacteria have an affinity for the protein and tear deposits on the surfaces of the lens matrix. In particular, the tears and fluids absorbed by the soft lenses serve as excellent bacterial culture media. If defects or nicks occur in the lens either during manufacture or subsequent patient wear, bacteria may find a haven to grow and be sheltered from superficial lens cleaning and disinfection.

Potentially harmful fungi also prove a possible danger to the soft contact lens. Fungi, like bacteria, can thrive in tear secretions or deposits and penetrate the lens material directly if enzymatic degradation of the lens material has taken place.

Other problems can accrue from incorrect and careless handling of the soft lenses by the patient himself. Many potential contaminants and lens deposits can be transferred from unwashed fingers to the surface of the soft lens. These include oily deposits from the skin, sweat, skin lotions and creams, mascara, detergents, lipstick and even nicotine. Controlled studies have demonstrated that bacterial contaminants occur in 43% of the makeup used by women, and fungal contaminants in 12%. Attempts to effect sterilization of the lenses by boiling, for example, can be cumbersome in addition to causing permanent damage to the lenses if done improperly. If the patient has used impure water for storage and rinsing of the lenses, undesirable deposits such as calcium, iron and insoluble divalent and trivalent metallic salts as well as other chemical deposits can collect on the lens surfaces.

Therefore, a need has arisen for an effective composition to counteract and mitigate the above described effects of improper hygiene and lens handling as well as to provide optimum disinfection and storage of the soft lens between lens wearing periods. In addition, the active ingredients of an effective contact lens solution should preferably: (1) disinfect clean soft lenses within a period of four to six hours and produce D values of a 90% kill rate of microorganisms, selected fungal and yeast organisms, and viral agents such as herpes simplex; (2) not be easily inactivated by small amounts of proteins, lipids or other tear and extraneous components and deposits; (3) not bind to protein or other lens surface deposits from the eye; and (4) not react with or absorb to the soft lens material or matrix. For example, several antiseptic agents which meet the above requirement for rapid and effective kill of a broad range of microorganisms have proved to be unsuitable for use in soft lens treatment solutions, in that these agents are incompatible with the soft lens material or bind with protein deposits on the surfaces of the lens matrix. Other antiseptic agents are unacceptable for use in soft lens solutions since they are concentrated by the lens material, to the extent that they cause discomfort and potential damage to the corneal surface of the wearer's eyes. Benzalkonium chloride is one such antiseptic agent which meets the requirements for effective and rapid killing of microorganisms but is unacceptable because it binds with many types of soft lens material and also binds with protein deposits on the lens surface.

One type of cold disinfecting solution for soft contact lenses uses chlorohexidine. However, chlorohexidine is absorbed by the soft contact lens material and gradually eluded into the eye often causing excessive burning, irritation and red eye, which can prevent the patient from wearing the lenses.

Therefore, a need has arisen for a highly effective cold storage and disinfecting solution for the overnight or interim disinfection and storage of soft and semi-hard contact lenses which meet the aforesaid requirements.

SUMMARY OF THE INVENTION

In accordance with the present invention, a storage and disinfecting solution containing ascorbic acid for the ambient temperature or cold storage and disinfection of soft and semi-hard contact lenses is provided. More particularly, the invention provides an effective ambient temperature storage and disinfecting solution for the disinfection and storage of hydrophilic gel lenses, semi-hard contact lenses and gelflex material soft lenses including, for example, the following plastic gel materials: hydroxyethyl methacrylate (HEMA) or its analogues, ethylene glycol dimethacrylate (EGMA) or its analogues, polymethyl methacrylate (PMMA) or its analogues, the relatively new semi-hard contact lens material cellulose-acetate-butyrate (CAB) and silicone polymers.

In one embodiment, the aqueous composition in accordance with the invention contains a disinfectant ascorbic acid compound that is present in an effective amount for killing bacteria. Suitable ascorbic acid compounds include ascorbic acid, disinfectant salts of ascorbic acid and mixtures thereof. Generally, an effective amount of the ascorbic acid compound is between about 0.1% and 20.0% calculated as ascorbic acid, by weight of the total composition.

An effective amount of a potentiating agent for enhancing the effectiveness of the ascorbic acid compound is preferably included, selected from the group consisting of trimethoprim and thimerosal. The combination of the ascorbic acid compound with a potentiating agent provides an ambient temperature disinfecting solution that is effective in killing microorganisms, fungal organisms and viral agents such as herpes simplex. Generally, the potentiating agent is present in an amount of between about 0.0001% and 5.0% by weight of the total composition.

The remainder of the composition may comprise solely water or may include various alkaline metal and alkaline earth metal water soluble salts to provide an aqueous composition salt content equivalent to about 0.8% to about 1.8% sodium chloride by weight of the total aqueous composition. A humectant such as propylene glycol may be optionally included in the composition. Further, a salt of ethylenediaminetetraacetic acid may be included as a buffering agent.

To provide a more stable composition, monothioglycerol may be included in the compositions of the present invention in an effective amount for stabilizing the ascorbic acid compound in the composition thereby increasing the shelf life of the composition.

The compounds present in the disinfectant composition may also be in kit form, in which a first component is provided that comprises the ascorbic acid compound preferably containing monothioglycerol and preferably formulated and packaged in an environment that is substantially devoid of free oxygen, and a second component that contains the other compounds present in the composition. At the time of intended use, the two components are mixed together to produce an ambient temperature soft contact lens disinfecting solution.

DETAILED DESCRIPTION OF THE INVENTION

The aqueous ambient temperature disinfecting compositions for soft and semi-hard contact lenses of the present invention contain a disinfectant ascorbic acid compound. Thus, the compositions in accordance with the invention act as a disinfectant for soft or semi-hard contact lenses without the necessity for heating. Suitable disinfectant ascorbic acid compounds include ascorbic acid, sodium ascorbate, calcium ascorbate and mixtures thereof. It is anticipated that other salts of ascorbic acid may also be effectively utilized as a disinfectant. As used herein, the term "disinfectant" means a substance that destroys or kills bacteria, fungi, yeasts or viruses. "Ascorbic acid" is equivalent to "L-ascorbic acid" or "L-xyloascorbic acid." Preferably, the ascorbic acid compound is present in the composition of the present invention as a sodium salt of ascorbic acid, sodium ascorbate. The ascorbic acid compound is present in the composition of the present invention in an amount sufficient to provide a disinfectant solution for soft contact lenses. Generally, the amount of ascorbic acid compound is present in an amount between 0.1% and 20% by weight of the total composition calculated as ascorbic acid. Thus, the actual weight percent of the ascorbic acid salt will be that weight percent of salt required to achieve a molar concentration of the ascorbic acid ion that is equal to the molar concentration of ascorbic acid at a given weight percent. For example, if it is desired to produce a solution of an ascorbic acid salt equivalent to 10% by weight ascorbic acid, the molar concentration "x," of a 10% by weight solution of ascorbic acid is computed. the weight percent of the ascorbic acid salt required to provide an ascorbic acid ion molar concentration of that amount, "x" is the actual weight percent of the ascorbic acid salt that is utilized. Preferably, ascorbic acid compound is present in an amount of about 10% by weight of the total composition, calculated as ascorbic acid. It is known that L-ascorbic acid is readily oxidized. Therefore, in accordance with the preferred embodiment of the invention the sodium salt of ascorbic acid is utilized, sodium ascorbate.

In D value studies to demonstrate the log kill of microorganisms, ascorbic acid at concentrations of 1.0% to 5.0% was shown to produce a significant log kill of 5 selected microorganisms, including *Psuedomonas aeruginosa* and *Stephylococcus aureus* within a six hour time period. Since ascorbic acid is naturally present in the human body and is nontoxic to ocular tissue in relatively large amounts, it is believed to be a safe and efficacious ingredient.

In the most preferred embodiment of the invention, monothioglycerol is included in an amount effective to stabilize the ascorbic acid compound. In the most preferred embodiment of the invention, monothioglycerol is present in a weight ratio of monothioglycerol to the ascorbic acid compound, calculated on the basis of ascorbic acid, of 1:50. Thus, for example, if the concentration of the ascorbic acid compound is 10%, calculated on the basis of ascorbic acid, the concentration of monothioglycerol is 0.2% by weight.

In order to enhance the disinfectant properties of the composition in accordance with the present invention, a potentiating agent, selected from the group consisting of, trimethoprim, also known as 2,4-Diamino-5-(3,4,5-Trimethoxy Benzyl) Pyrimidine, and thimerosal, is preferably included in an effective amount for providing a disinfectant composition in combination with an ascorbic acid compound for enhancing the D value kill factor relating to bacteria, fungus, yeast and viral organisms. Generally, an effective amount of the potentiating agent is between about 0.0001% and 5.0% by weight of the total composition. Preferably, the potentiating agent is present in an amount of about 0.005% by weight of the total composition.

In order to further increase the shelf life, the compositions are formulated and packaged in an atmosphere that is substantially devoid of free oxygen. For example, the compositions can be formulated and sealed in sterile containers, in the presence of a nitrogen or carbon dioxide atmosphere. Further, it is advantageous for the ascorbic acid compound to be packaged in a non-transparent container to reduce degradation that can be caused by ultraviolet radiation.

The compositions of the present invention preferably include at least one essentially neutral water-soluble compatible salt to provide tonicity equivalent to between about 0.8% and 1.8% sodium chloride by weight of the total aqueous composition. Thus, the preferred compositions according to the invention provide a tonicity which is about the same as or slightly higher than the tonicity of normal human tear fluid. While hypertonic solutions can be desirable since the solution will have a greater osmotic pressure than that of the tear fluid of the contact lens wearer, any soluble salts or mixtures of salts, compatible with ocular tissue, can be used to provide the desired tonicity. Preferably, sodium chloride, potassium chloride or mixtures thereof, are used to provide the desired tonicity. It is understood, however, that one or more essentially neutral, water-soluble alkali or alkaline earth metal salts can be substituted in whole or in part for the sodium or potassium chloride in the solutions of the invention, when tonicity adjustment is desired. Preferably, sodium chloride and potassium chloride are combined together in a weight ratio of between about 2:1 and 7:3, respectively.

A salt of ethylenediaminetetraacetic acid may be included as a buffering agent for the ambient temperature disinfectant solution of the invention for maintaining the pH of the composition in an acid range, preferably between about 4.0 and 7.0. Further, salts of ethylenediaminetetraacetic acid have also been demonstrated to have antibacterial and antifungal properties. The preferred salt of ethylenediaminetetraacetic acid is disodium ethylenediaminetetraacetate, and is preferably present in a concentration of from about 0.05% to about 2.0% by weight of the total aqueous composition and most preferably present in an amount of about 0.1% by weight of the total aqueous composition.

Propylene glycol may optionally be included in the compositions, generally in an amount between about 0.2% and about 2.5% by weight of the total aqueous composition and preferably in an amount of about 0.70% by weight of the total aqueous composition. The propylene glycol acts as a humectant, preservative and fungal growth inhibitor.

In accordance with a preferred embodiment of the present invention, the ascorbic acid compound is utilized together with monothioglycerol and these two compounds are separated from the other components present in the total composition until the time of intended use. Water may or may not be included in the combination of the ascorbic acid compound and monothioglycerol. Thus, the ambient temperature disinfecting composition can be packaged in kit form in which a first component containing a mixture of the ascorbic acid compound, in solid form, partially or completely dissolved in water, and monothioglycerol can be formulated and packaged in a sealed sterile container, preferably packaged in an environment substantially free of free oxygen, such as a carbon dioxide or nitrogen atmosphere. A second component containing water and other compounds that may be present in the composition are contained in a second container. When one desires to use the disinfectant solution, the two components can be mixed together and utilized.

The aqueous composition in accordance with the invention is preferably utilized as part of the total patient regimen for maintaining and treating soft, silicone and semi-hard lenses. Thus, an effective cleaning step or steps is an important part of any effective soft or semi-hard lens treatment and maintenance regimen. Separate cleaning of the lenses insures that the disinfectant properties of the aqueous solution will not be overwhelmed by gross organic or inorganic deposits and pollutants.

Whereas the present invention has been described with respect to specific embodiments, it will be understood that various changes and modifications will be suggested to one skilled in the art and it is intended that the invention encompass such changes and modifications as fall within the scope of the appended claims.

I claim:

1. An aqueous composition which disinfects soft and semi-hard contact lenses at ambient temperature consisting essentially of:

water, a first compound selected from the group consisting of ascorbic acid, sodium ascorbate, calcium ascorbate and mixtures thereof, said first component present in an amount of between about 0.1% and 20% by weight of said total aqueous composition calculated as ascorbic acid, and a second compound selected from the group consisting of trimethoprim and thimerosal, said second compound present in an amount of between about 0.0001% and 5.0% by weight of said total aqueous composition, said aqueous composition being compatible with soft contact lenses to allow storage of soft contact lenses therein.

2. The aqueous composition as recited in claim 1 wherein said second compound is present in an amount of about 0.005% by weight of the total aqueous composition.

3. The aqueous composition as recited in claims 1 or 2 wherein said first compound is present in an amount of about 10% by weight of the total aqueous composition, calculated as ascorbic acid.

4. The aqueous composition as recited in claim 1 wherein said first compound is sodium ascorbate.

5. The aqueous composition as recited in claims 1, 2 or 4 wherein said second compound is thimerosal.

6. The aqueous composition as recited in claims 1, 2 or 4 wherein said second component is trimethoprim.

7. The aqueous composition as recited in claim 1 further consisting essentially of monothioglycerol present in an effective amount for stabilizing said first compound.

8. The aqueous composition as recited in claim 7 wherein said monothioglycerol is present in a weight ratio of monothioglycerol to said first compound calculated as ascorbic acid of about 1:50.

9. The aqueous composition as recited in claim 1 further consisting essentially of propylene glycol present in an amount of between about 0.2% and 2.5% by weight of the total aqueous composition.

10. The aqueous composition as recited in claim 1 further consisting essentially of disodium ethylenediaminetetraacetate present in an effective amount for maintaining the pH of the aqueous composition in the range of between about 4.0 and 7.0.

* * * * *

REEXAMINATION CERTIFICATE (350th)
United States Patent [19]
Sherman

[11] B1 4,367,157

[45] Certificate Issued * May 14, 1985

[54] SOFT CONTACT LENS AMBIENT TEMPERATURE DISINFECTANT SOLUTION CONTAINING ASCORBIC ACID OR SALT THEREOF

[75] Inventor: Guy J. Sherman, Mandeville, La.

[73] Assignee: Sherman Laboratories, Inc., Abita Springs, La.

Reexamination Request:
No. 90/000,550, May 2, 1984

Reexamination Certificate for:
Patent No.: 4,367,157
Issued: Jan. 4, 1983
Appl. No.: 228,562
Filed: Jan. 26, 1981

[ * ] Notice: The portion of the term of this patent subsequent to Oct. 26, 1999 has been disclaimed.

Related U.S. Application Data

[63] Continuation-in-part of Ser. No. 37,645, May 10, 1979.

[51] Int. Cl.$^3$ .................. C11D 3/48; C11D 1/04
[52] U.S. Cl. .................. 252/106; 252/173; 252/546; 252/DIG. 14
[58] Field of Search ....... 252/106, 173, 546, DIG. 14; 424/141, 146, 280

[56] References Cited

U.S. PATENT DOCUMENTS

| | | | |
|---|---|---|---|
| 3,065,139 | 11/1962 | Ericsson et al. | 424/317 |
| 3,639,576 | 2/1972 | Kaspar et al. | 424/78 |
| 3,681,492 | 8/1972 | Kotzbauer | 424/141 |
| 3,755,561 | 8/1973 | Rankin | 424/78 |
| 3,888,782 | 6/1975 | Boghosian et al. | 252/106 |

FOREIGN PATENT DOCUMENTS 110055  9/1974  Japan .

*Primary Examiner*—P. E. Willis, Jr.

[57] ABSTRACT

Aqueous compositions for the ambient temperature or cold disinfection of soft contact lenses during non-wearing periods is provided. The composition includes water and a disinfectant composition comprising an effective amount of an ascorbic acid compound for killing bacteria, generally between about 0.1% and 20% by weight of the total aqueous composition, calculated as ascorbic acid. The disinfectant composition may also include a potentiating agent to further enhance the kill factor of ascorbic acid with respect to fungi, yeasts and viruses.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 6–8 is confirmed.

Claims 1–5, 9 and 10 are cancelled.

* * * * *